United States Patent [19]
McGee

[11] Patent Number: 5,414,268
[45] Date of Patent: May 9, 1995

[54] LIGHT SCANNER WITH INTERLACED CAMERA FIELDS AND PARALLEL LIGHT BEAMS

[75] Inventor: Arthur L. McGee, Lake Oswego, Oreg.

[73] Assignee: The Coe Manufacturing Company, Portland, Oreg.

[21] Appl. No.: 189,797

[22] Filed: Feb. 1, 1994

[51] Int. Cl.[6] ............................................. G01N 21/30
[52] U.S. Cl. ...................................... 250/560; 356/376
[58] Field of Search .................... 250/560, 561, 223 R; 356/376, 381, 384, 383, 385, 386, 387

[56] References Cited

U.S. PATENT DOCUMENTS

| | | | |
|---|---|---|---|
| 3,983,403 | 9/1976 | Dahlström et al. | 250/560 |
| 4,152,767 | 5/1979 | Laliotis | 250/560 |
| 4,301,373 | 11/1981 | Sjödin | 250/560 |
| 4,803,371 | 2/1989 | Durland | 250/560 |

OTHER PUBLICATIONS

"DynaVision II—for edger/trimmer/cant optimizer" advertisement of Dynamic Control Systems of Delta, British Columbia, Canada, in *Timber Processing*, Mar. 1994, p. 9.

*Primary Examiner*—David C. Nelms
*Assistant Examiner*—John R. Lee
*Attorney, Agent, or Firm*—Klarquist Sparkman Campbell Leigh & Whinston

[57] ABSTRACT

A light scanner for determining the configuration of elongated objects, such as logs or lumber, is described. The object is moved laterally through the scanner past a plurality of laser light sources and a plurality of photo-detector cameras spaced along the object. The coherent laser light beams are parallel to each other and to the lens axis centerline of the cameras for easier alignment and to prevent the laser light spot on the object from moving relative to such axis centerline for objects of different thickness. The cameras have a photo-detector target which may be a linear diode aray CCD semiconductor device for producing scan data signals in response to reflected light beams which are processed by a computer system giving preference to the data produced by the beams in the outer portions of the camera viewing field to determine the thickness of the object at points spaced along the object. Non-coherent polychromatic light is also reflected from the object to the cameras to detect the ends of the object and to determine its length. Reference targets are provided along one side of the object to sense the leading end and the trailing edge of the object as it is moved laterally to block light reflected from or emitted by such targets to the cameras on the opposite side of the object.

20 Claims, 6 Drawing Sheets

LIGHT SCANNER WITH INTERLACED CAMERA FIELDS AND PARALLEL LIGHT BEAMS

The present invention relates generally to light scanner apparatus and methods for scanning elongated objects such as logs, lumber, or other wood products to determine the configuration of such objects, and in particular, to such a light scanner employing parallel light beams and a plurality of photo-detector cameras whose viewing fields are interlaced with adjacent cameras having viewing fields partially overlapping. The light scanner apparatus and method of the invention determine the thickness of the elongated object by selective use of the scanning output data of the cameras produced by laser light beams reflected from the object to the cameras which gives preference to the data produced by sensing light beams in outer field portions remote from the optical axis of the camera compared to data produced by light beams in inner field portions adjacent the optical axis, for greater thickness measurement accuracy.

The scanning apparatus and method of the present invention is especially useful in determining the configuration of logs, partially finished lumber or "cants", and other wood products.

BACKGROUND OF THE INVENTION

It has been previously proposed in U.S. Pat. No. 4,803,371 to Durland, issued Feb. 7, 1989, to provide an optical scanning method and apparatus for determining the configuration of an elongated object using both non-coherent or "white" light and coherent laser light simultaneously in order to determine both the length of the object and its thickness. In this prior scanner the laser light beams are positioned at different angles with respect to each other and to the optical axis of the photo-detector camera which has the disadvantage that it is difficult to align the laser light beams properly. Also, the laser beam spot on the object changes in position relative to the centerline of the camera field with changes in thickness of the object. These problems are avoided in the present invention by employing laser light beams which are aligned parallel to each other and to the optical axis of the camera which enables them to be more easily aligned and also enables the laser spot position on the object to remain substantially constant in spite of changes in thickness of the object being measured.

It has been found that when using laser light beams which are parallel to the axis of the camera viewing fields, the thickness determinations made from scan data produced by the photo-detector camera for light beams in the inner zone portions of the optical field adjacent the axis of the camera have extremely low accuracy due to the small change in the angle of the reflected laser beams for changes in thickness of the object. However, scan data obtained by the camera for light beams in the outer zone portions of the viewing field more remote from the optical axis produces thickness determinations having a much greater accuracy due to the larger change in angle of the reflected laser beams when striking objects of different thicknesses.

The light scanner apparatus and method of the present invention overcomes the above-discussed problems by employing laser light beams which are positioned parallel to the optical axis of the camera, by interlacing the camera viewing fields to partially overlap the fields of adjacent cameras which are spaced along the entire length of the object and by using only the scan data produced by reflected laser beams in the outer zones of the viewing field remote from the optical axis to measure object thickness changes with greater accuracy. Thus, the scan data corresponding to reflected laser beams in the inner field zones adjacent the optical axis of the camera is only used to measure the thickness of the object when the scan data corresponding to the outer zones is unavailable or defective for a particular camera.

The optical scanning apparatus of the present invention may employ a photoelectric sensor array as the target of the camera in order to convert the light reflected from the surface of the log or other elongated object into electrical scan data signals indicating the thickness of the object. As discussed in the above-referenced Durland patent, the photoelectric sensor may be in the form of a linear diode array including a plurality of PN junction semiconductor diodes which are positioned in a straight line and may be charge coupled together to provide a charge coupled semiconductor device (CCD). This photo-detector sensor measures the thickness of the elongated object by sensing the position of the reflected laser light spot on the linear diode array to indicate such thickness. The position of the light spot on the array corresponds to the distance that the surface of the object is spaced from the camera lens which may be determined mathematically in the manner described in connection with FIG. 4 of the Durland patent. As a result of employing a linear diode array which typically consists of an array of 1024 diodes spaced along a target length of about 0.5" or 13.3 mm so that the size of one individual diode and the change in position of the light spot on such array determine the smallest detectable change in laser dot position on the object and corresponding thickness change of the object. Since the amount of the change in the angle of the reflected laser light beam reflected from the surface of the object to the camera lens due to differences in the thickness of the object determines the change of spot position on the array, a large angle change is extremely important for accurate measurement of the thickness of such object.

SUMMARY OF THE INVENTION

It is therefore one object of the present invention to provide an improved light scanner apparatus and method for determining the configuration of an elongated object with a plurality of parallel laser light beams which are aligned parallel to the optical axes of a plurality of photo-detector cameras spaced along such object to detect such light beams for rapid scanning, easier alignment and accurate measurement of the object configuration.

Another object of the invention is to provide such an improved light scanning apparatus and method in which the photo-detector cameras have their viewing fields interlaced so that portions of adjacent viewing fields overlap in order to enable preferential use of scan data produced by a camera in response to the parallel laser light beams reflected from the object in the outer portions of the viewing field rather than the scan data signals produced by light beams in the inner portions of the viewing field adjacent the optical axis of the camera, for producing thickness measurements of the object with greater accuracy.

A further object of the present invention is to provide such an improved light scanner apparatus and method in which the scan output signal data is selectively processed by a computer giving preference to the scan data produced by laser light beams in the outer zones of the viewing field while rejecting the scan data produced by laser light beams in the inner zones of such viewing field and overlapping the viewing fields of adjacent cameras to produce thickness measurement signals from all of the laser beams spaced along the entire length of the elongated object for determining the surface configuration of the object with high accuracy.

An additional object of the invention is to provide such an improved light scanner apparatus and method in which lighted reference targets are provided on one side of a scanning zone so that such targets are normally seen by the cameras on the opposite side of the scanning zone but are blocked by the object when the object moves laterally through such beams in order to detect the top leading edge and bottom trailing edge of the object by the lasers on the same side as the cameras.

Still another object of the present invention is to provide such an improved light scanner apparatus and method in which a plurality of non-coherent light sources are spaced along the scanning zone for illuminating the elongated object with non-coherent light which is reflected from the object to at least some of the photo-detector cameras so they produce an output signal of lower amplitude than the laser beams to detect the opposite ends of the object and thereby determine the length of such object.

A still further object of the invention is to provide such a light scanner in which the parallel laser beams are spaced apart sufficiently to provide a gap between adjacent beams over the full range of scan depth so that only one beam is detected by each portion of a linear diode array in the photo-detector of each camera over the range of thickness within the scan depth of the camera lens system to produce thickness measurements of great accuracy.

BRIEF DESCRIPTION OF THE DRAWINGS

Other objects and advantages of the present invention will be apparent from the following detailed description of a preferred embodiment thereof and from the attached drawings of which

DETAILED DESCRIPTION OF THE PREFERRED EMBODIMENT

Figure 1:
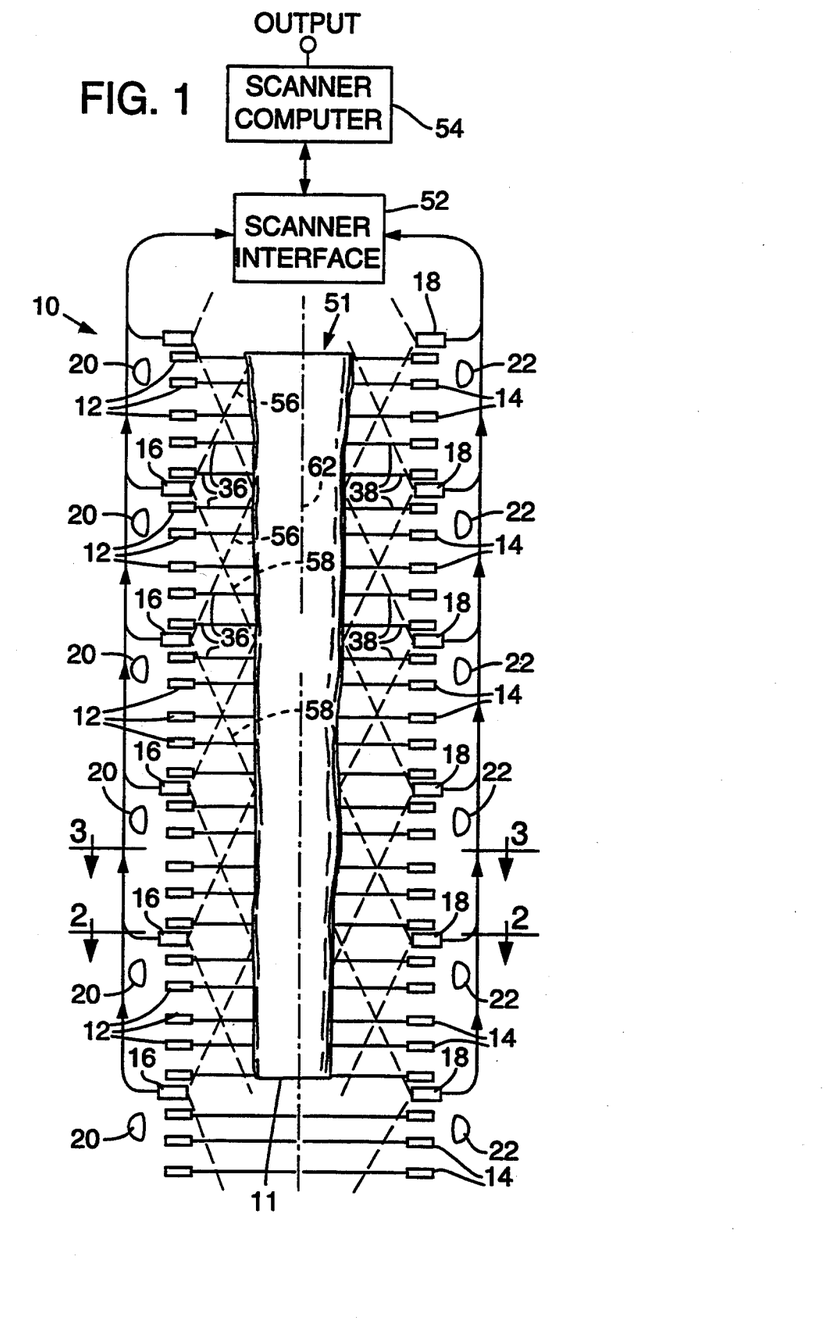
FIG. 1 is a schematic plan view of the scanner apparatus of the present invention with associated electrical signal processing circuit.
Figure 2:
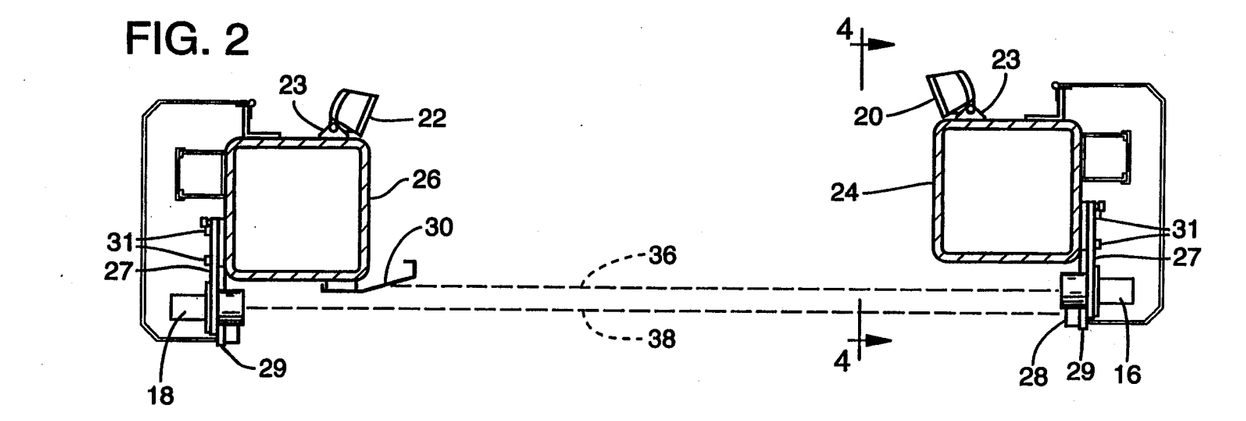
FIG. 2 is an enlarged horizontal section view taken along line 2—2.
Figure 4:
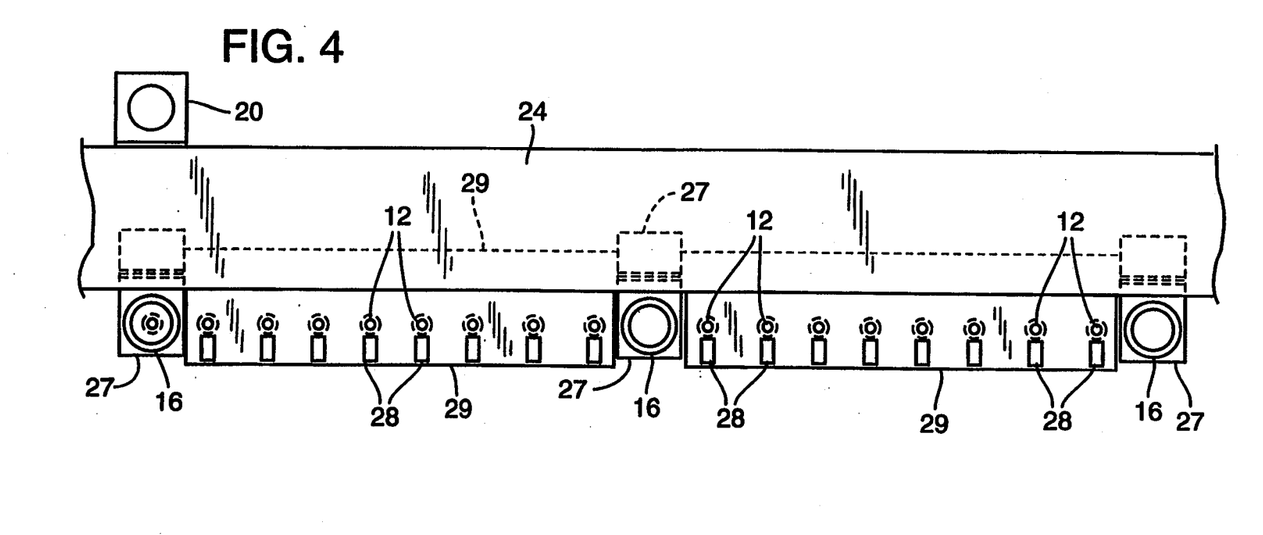
FIG. 4 is an enlarged vertical section view taken along line 4—4 of FIG. 2.

As shown in FIGS. 1, 2 and 4, the light scanner apparatus of the present invention includes a photo-detector light scanner 10 for scanning a log 11 or other elongated object as it moves through the scanner to determine the three-dimensional configuration of such object. The scanner 10 includes a plurality of first laser light sources 12 positioned in spaced relationship along one side of the log when such log is moved through the scanner, and a plurality of second laser light sources 14 positioned in spaced relationship along the opposite side of the log. The laser light sources 12, 14 may be continuous emission gas lasers which emit narrow beams 36 and 38, respectively, of coherent laser light. The scanner also includes a first set of photo-detector cameras 16 mounted in spaced relationship along one side of the log and a second set of cameras 18 mounted in spaced relationship along the opposite side of the log. It should be noted that the adjacent pairs of cameras on the same side of the log are separated by a plurality of laser light sources and the viewing fields of adjacent pairs of cameras overlap to cover several laser light sources on both sides of the camera, as hereafter described with respect to FIG. 5.

Figure 3:
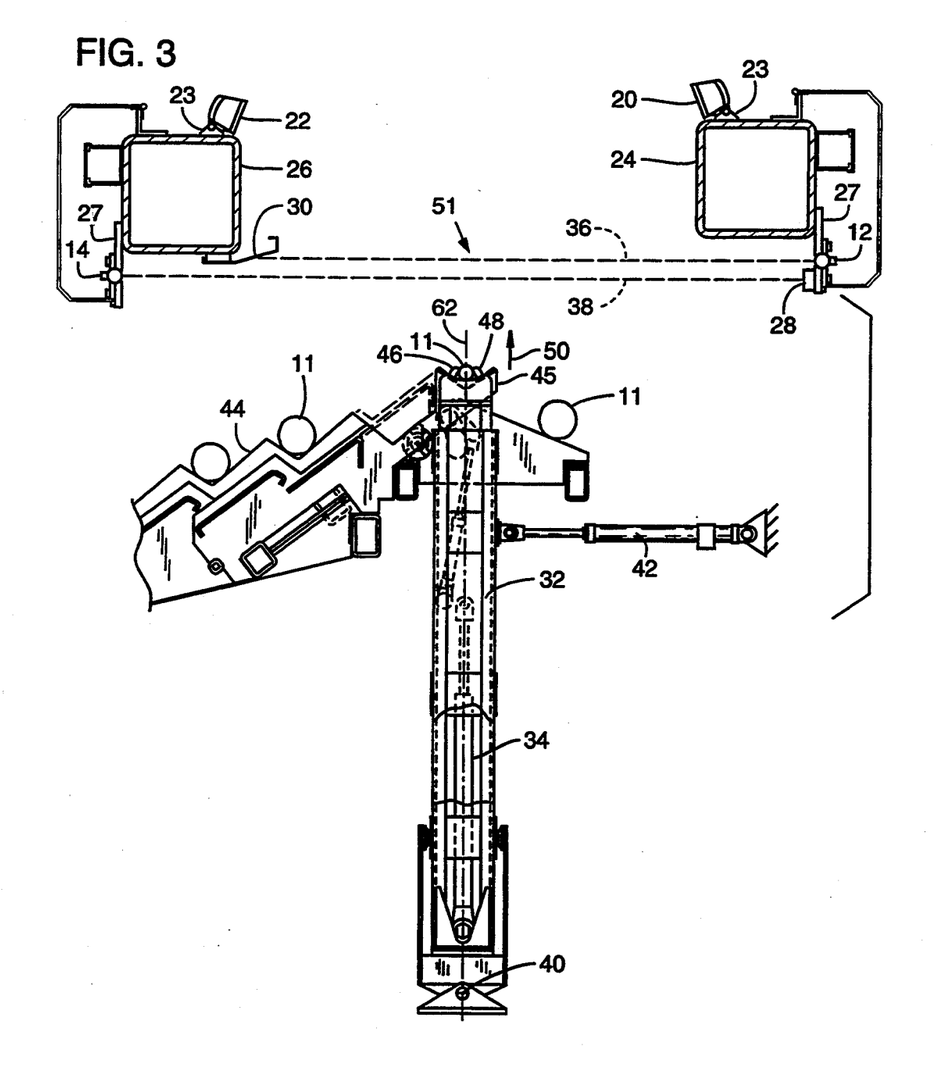
FIG. 3 is an enlarged horizontal view taken along line 3—3 of FIG. 1 and also shows log transport mechanism for moving the log through the scanner light beams in order to determine the configuration of the log.

As shown in FIGS. 1 and 2, a plurality of non-coherent, polychromatic or "white" light sources are positioned on at least one side of the log 11 to measure its length, and are preferably provided in two groups 20 and 22 on opposite sides of the log 11 and spaced along the log which may have a length of between about 8'-20'. The non-coherent light sources 20, 22 emit non-coherent diffused light of lower intensity than the laser light. This non-coherent light is reflected from the elongated object to the cameras 16, 18 in order to detect the position of the inner and outer ends of the log for determining the length of the log in a similar manner to that described in U.S. Pat. No. 4,803,371 to Durland, issued Feb. 7, 1989 whose disclosure is hereby incorporated by reference. The non-coherent lights 20, 22 may be halogen lamps which are mounted by brackets 23 upon a pair of support beams 24, 26 positioned on opposite sides of a log scanning zone 51 through which the log is raised as shown in FIGS. 2 and 3. The photo-detector cameras 16, 18 and the laser lights 12, 14 are also supported by mounting plates 27 and 29, respectively, on support beams 24, 26 with bolts 31.

A plurality of white colored reference targets 28 are supported on mounting members 29 attached to the support beam 24, beneath the light sources 12 in order to reflect laser light beams 38 emitted by lasers 14 back to the cameras 18, as shown in FIG. 4. The reference targets 28 are employed along with the laser light sources 14 and cameras 18 to sense when the light beams 38 are blocked by the log and no longer reflected by the targets 28 back to the cameras. This enables the scanner to detect the leading edge of the log and the trailing edge of the log as it is moved laterally upward through a scanning zone 51 of scanner 10 between the two banks of light sources and cameras by charger arms 32 as hereafter described with respect to FIG. 3.

A light beam deflector member 30 is positioned on the opposite side of the scanner from the other laser light sources 12 and reference targets 28 in order to deflect the laser light beams 36 emitted by light sources 12 downward and away from the cameras when no log or other elongated object is present in the scanning zone 51 to avoid stray reflections into the cameras.

As shown in FIG. 3 for scanning, the log 11 is held adjacent its opposite ends by a selected pair of charger arms 32 which are adjusted in length by means of extension cylinders 34 to raise the log upward along a centerline 62 of the charger in a lateral direction to its longitudinal axis through scanning zone 51. Logs 11 are conveyed upward to the charger arms by a log feeder 44 in stair steps until they reach V-shaped holders 45 at the top of the feeder where the log is clamped between a pair of gripping fingers 46, 48 at the end of each charger arm 32. The log is then moved laterally upward in the direction of arrow 50 by extension of the charger arms 32 under the control of extension cylinders 34. As a result, the log passes through the light beams 36, 38 of the laser light sources in order to scan the log and determine its configuration by means of the photoelectric cameras 16, 18. During such scanning the log intersects and passes through the light beams 36 emitted by the first laser light sources 12 and the light beams 38 emitted by the second set of laser light sources 14 and causes the beams to be reflected to cameras 16, 18 to determine the thickness and length of the log at each beam. After the log is scanned, the charger arms 32 are pivoted about pivot point 40 at the bottom end of such charger arms for transferring the log to a sawmill log carriage (not shown) by means of a pair of pivot cylinders 42. Each of the cylinders 42 has one end connected to a fixed pivot and its other end pivotally connected by its piston rod to the charger arm.

As shown in FIG. 1, the analog scan data output signals of the cameras 16, 18 are transmitted to a scanner interface circuit 52 which includes a plurality of individual camera interface circuits similar to that shown in FIG. 10 of above-referenced U.S. Pat. No. 4,803,371 to Durland. These camera interface circuits convert the analog scan data output signals of the cameras to digital scan data signals which are transmitted to a scanner computer system 54 for processing the data signals to determine the configuration of the log. The scanner computer system 54 may be similar to that shown in FIG. 11 of the above-cited Durland patent.

It should be noted that each of the photo-detector cameras 16, 18 has a photoelectric target which may be in the form of a linear diode array consisting of 1024 semiconductor diodes connected together as a charge coupled semiconductor device (CCD). The location of the position of the light spots corresponding to laser light beams 36, 38 on the photoelectric target is an indication of the distance from the lasers 12, 14 to laser light spot on the elongated object. This measured distance is used to determine the thickness of the object at that point by trigonometry in a manner similar to that shown in the Durland patent as hereafter described with respect to FIG. 7. It should be noted that the camera output scan data signal produced by each diode in the linear diode array CCD target is identified as to its position on the array by an address output signal of a counter in the camera interface circuit which is connected to the output of a clock oscillator pulse generator for controlling the CCD control logic circuit as shown in FIG. 10 of the above-cited Durland patent. In this manner, the location of the laser beam spot in field of view of the camera including whether it is located in an outer field portion or an inner field portion is determined for data processing in a manner hereafter described.

Figure 5:
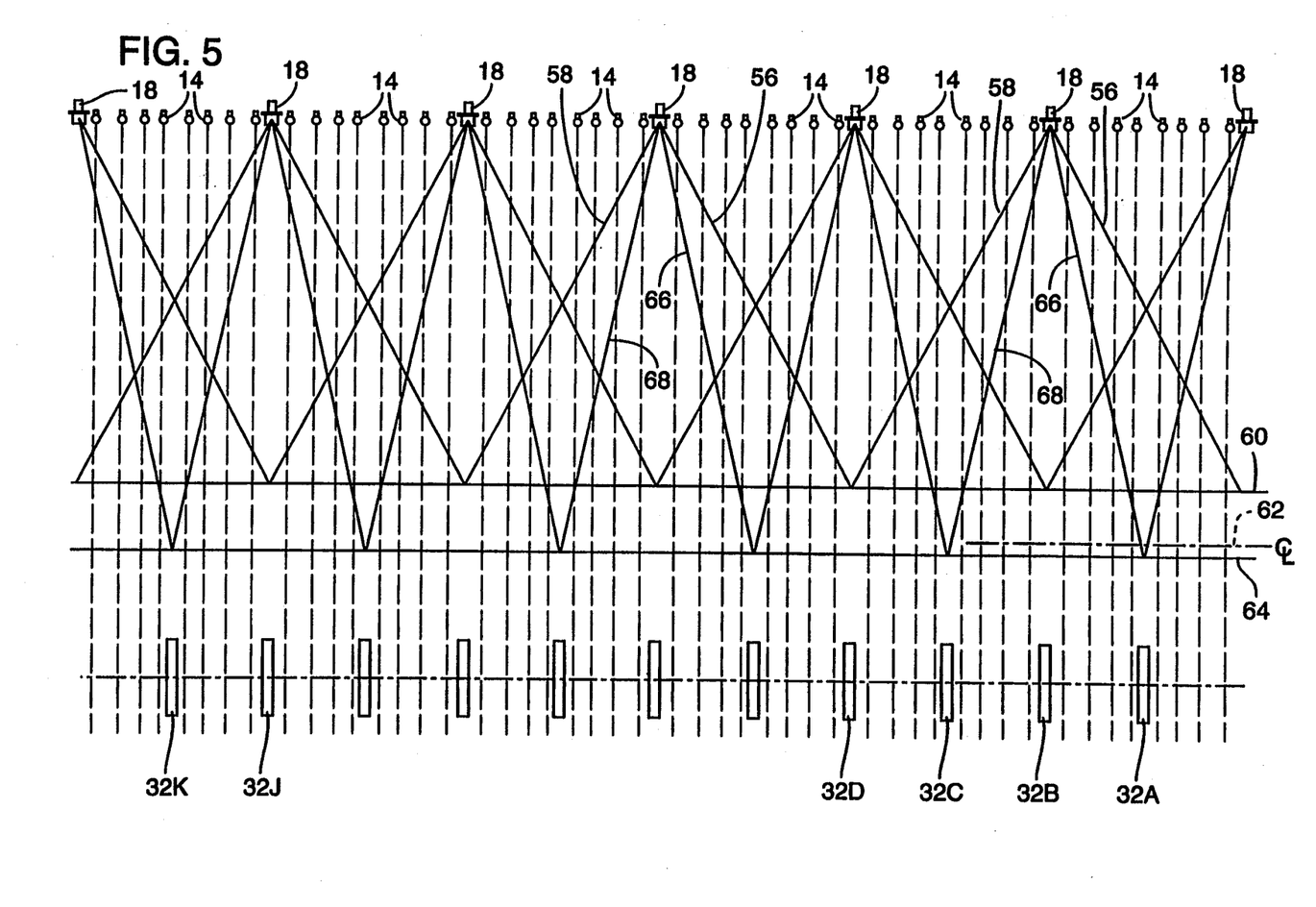
FIG. 5 is a schematic diagram showing the positions of the laser light sources and the cameras together with the light beams emitted by such lasers and the overlapping viewing fields of the cameras on one side of the scanner of FIGS. 1-4.

As shown for cameras 18 in FIG. 5, each of the cameras 16, 18 is provided with a first viewing field extending between field boundary lines 56, 58 when the lenses of the cameras are focused at the inner limit of the depth of field of such lenses on a first limit object plane 60 spaced about 15" outward from the centerline 62 of the charger. The lenses of the cameras 16, 18 may also be focused at the outer limit of the depth of field of such lenses on a second limit object plane 64 about 2" on the opposite side of the centerline 62 from plane 60, in which case the outer boundary limits of the second viewing field are indicated by boundary lines 66, 68. Thus, for a typical camera lens the depth of field of focus within which objects are in focus extends from reference plane 64 to plane 60 or over a distance (15"+2") of about 17". As a result the preferred embodiment of the light scanner of the present invention can determine the configuration of logs having a radius in the range of 0"–15" or a maximum diameter of 30". Actually the maximum diameter log which can be measured is somewhat less than 30" because of the irregular surface of the side of the log. The cameras 16, 18 are all spaced 92.2" from the centerline 62 of the charger and are each spaced from the adjacent cameras of its group by about 42"–48". The laser light sources 12, 14 are also spaced 92.2" from centerline 62 and when eight lasers are provided between each pair of cameras such lasers are spaced from the adjacent laser by about $4\frac{1}{4}$" to $5\frac{3}{4}$" except for the pair of lasers on opposite sides of each camera which are spaced apart by $7\frac{3}{4}$".

The horizontal positions of the different pairs of charger arms 32 are shown at positions 32A–32K in FIG. 5 with respect to the spacing between the laser light sources 14 and the cameras 18. It should be noted that there are eight laser light sources between each adjacent pair of cameras 16, 18 one half of the charger arms 32 are positioned in alignment with the cameras and the other half are in alignment with the space between the fourth and fifth laser light sources between the cameras. Only one pair out of the eleven charger arms 32A–32K are used at one time and such pair is selected depending upon the length of the log. It should be noted that the actual vertical position of the charger arms in FIG. 5 is beneath the centerline 62 of the charger and they are shown displaced from such centerline for clarity so that only the horizontal position of the charger arms is accurately shown in FIG. 5.

Figure 7:
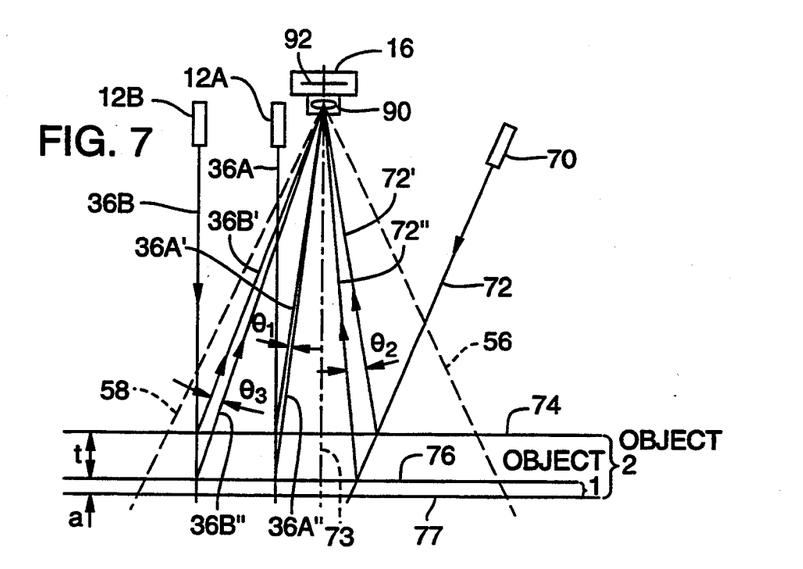
FIG. 7 is a schematic diagram showing a prior art scanner and comparing it with the scanner of the present invention.

As shown in FIG. 7, with the previous scanner of the Durland patent a plurality of angled laser light sources 70 are employed each with its light beam axis 72 at an acute angle relative to the lens axis centerline 73 of the camera 16. In contrast the laser light sources 12A, 12B of the scanner of the present invention have parallel light beams 36A, 36B which are parallel to the centerline axis 73. However, first light beam 36A near the axis 73 produces only a small difference angle $\Theta_1$ between reflected beam 36A' reflected from the second object 74 and the reflected beam 36A" from the first object 76. As a result of the acute angle of beam 72, a larger difference angle $\Theta_2$ is produced between the reflected light beam 72" reflected from the outer surface 74 of a thick second object and the reflected beam 72" reflected from the upper surface of a thinner first object 76. For purposes of explanation, both objects are assumed to be resting on the same reference plane 77 and the first object has a thickness "a" and the second object has a thickness "a+t". This large difference angle $\Theta_2$ enables more accurate measurement of the thickness difference "t" between the first object 76 and the second object 74. However, this prior scanner has the disadvantages that it is very difficult to align the acute angled beams 72 of laser light sources 70 and the distance of the laser spots on the object surfaces 74, 76 from the camera lens centerline or axis 73 changes with changes in object thickness as shown in FIG. 7.

To overcome these problems, the scanner of the present invention employs parallel laser beam light sources including lasers 12A, 12B which emit light beams 36A, 36B parallel to the centerline or optical axis 73 of the camera 16. This enables easier alignment of such light beams and the position of the laser beam spot on the object does not change with objects of different thickness. However, with the present scanner the laser light sources close to the axis 73 of the camera, such as light source 12A, the difference angle $\Theta_1$ between the reflected light beams 36A', 36A", respectively, reflected by the top surface 74 of object 2 and from the upper surface 76 of object 1 is an extremely small angle as discussed above. This small difference angle $\Theta_1$ makes it difficult for the camera 16 to accurately measure the difference in thickness "t" between object 1 and object 2 using light beam 36A near the lens axis centerline 73. As the laser light source is positioned a greater distance from the centerline 73 of the camera lens, such as laser source 12B, the difference angle $\Theta_3$ for reflection of its light beam 36B increases in size to a more acceptable magnitude for accurate measurement of the thickness difference "t". Thus the reflected light beam 36B' which is reflected from the upper surface 74 of object 2 and the reflected light beam 36B" reflected from the surface 76 of object 1 have a difference angle $\Theta_3$ which is larger than $\Theta_1$, thereby making the thickness difference "t" more easily measured by the camera. It should be noted that the difference angle $\Theta_3$ of the second light source 12B from the axis centerline 73 is still less than the difference angle $\Theta_2$ of the angled light source 70 even though its spot is spaced more than twice the distance than such angled light source from the axis.

Figure 8:
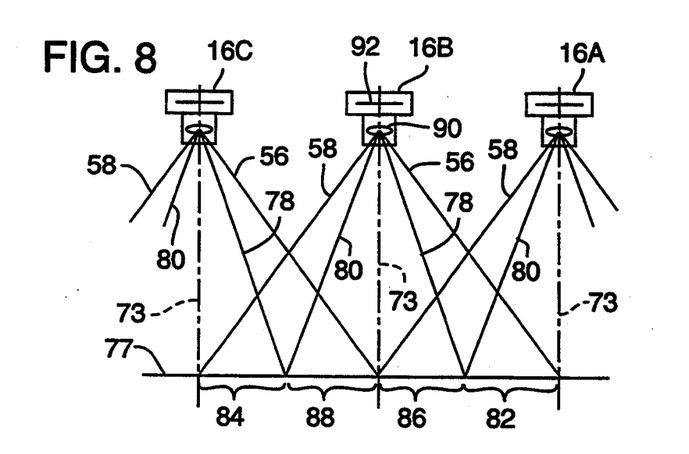
FIG. 8 shows the overlapping fields of the cameras used in the scanner of the present invention.

In order to achieve more accurate measurement of thickness differences, the scanner of the present invention employs selective data processing giving preference to scan data produced by laser light beams located in the two outer portions or zones of the camera viewing field, as hereafter discussed. The plurality of photodetector cameras 16, 18 include adjacent pairs of cameras having fields of view which overlap. As shown in FIG. 8, the viewing field of each of the three cameras 16A, 16B and 16C which is defined by outer boundary lines 56, 58 overlaps the viewing field of the adjacent cameras on opposite sides thereof. Thus, the right boundary 56 of the field for camera 16C overlaps the field of camera 16B and intersects the centerline 73 of camera 16B at reference plane 77. Also the left outer boundary 58 of the viewing field of camera 16A partially overlaps the field of camera 16B and intersects the centerline 73 of the camera 16B at plane 77.

An inner field portion of the camera viewing field defined by boundary limits 78, 80 is that closest to the centerline 73 of the camera and includes a right inner zone from 78-73 and a left inner zone from 80-73. It should be noted that the left boundary 80 of the inner viewing field portion of camera 16A intersects the right boundary 78 of the inner viewing field of camera 16B at plane 77 approximately half way between the cameras. Similarly, the right boundary 78 of the inner viewing field portion of camera 16C intersects the left boundary 80 of the inner viewing field of camera 16B at plane 77. As stated above the left outer field boundary line 58 of camera 16A intersects the right outer field boundary line 56 of camera 16C at a point on the plane 77 where the axis 73 of camera 16B intersects such plane. As a result, the entire length of the object plane 76 is covered without gaps by outer viewing field zones, as hereafter described. Thus the center camera 16B has a right outer field zone 82 between lines 56 and 78 on plane 77 and a left outer field zone 84 between lines 58 and 80. Similarly, camera 16A has a left outer zone 86 between lines 58 and 80 and camera 16C has a right outer zone 88 between lines 56 and 78. Thus, the inner field zones 86, 88 of camera 16B are also outer field zones of cameras 16A and 16C so that the entire length of the reference plane 77 may be covered by only outer field zones.

Figure 9:
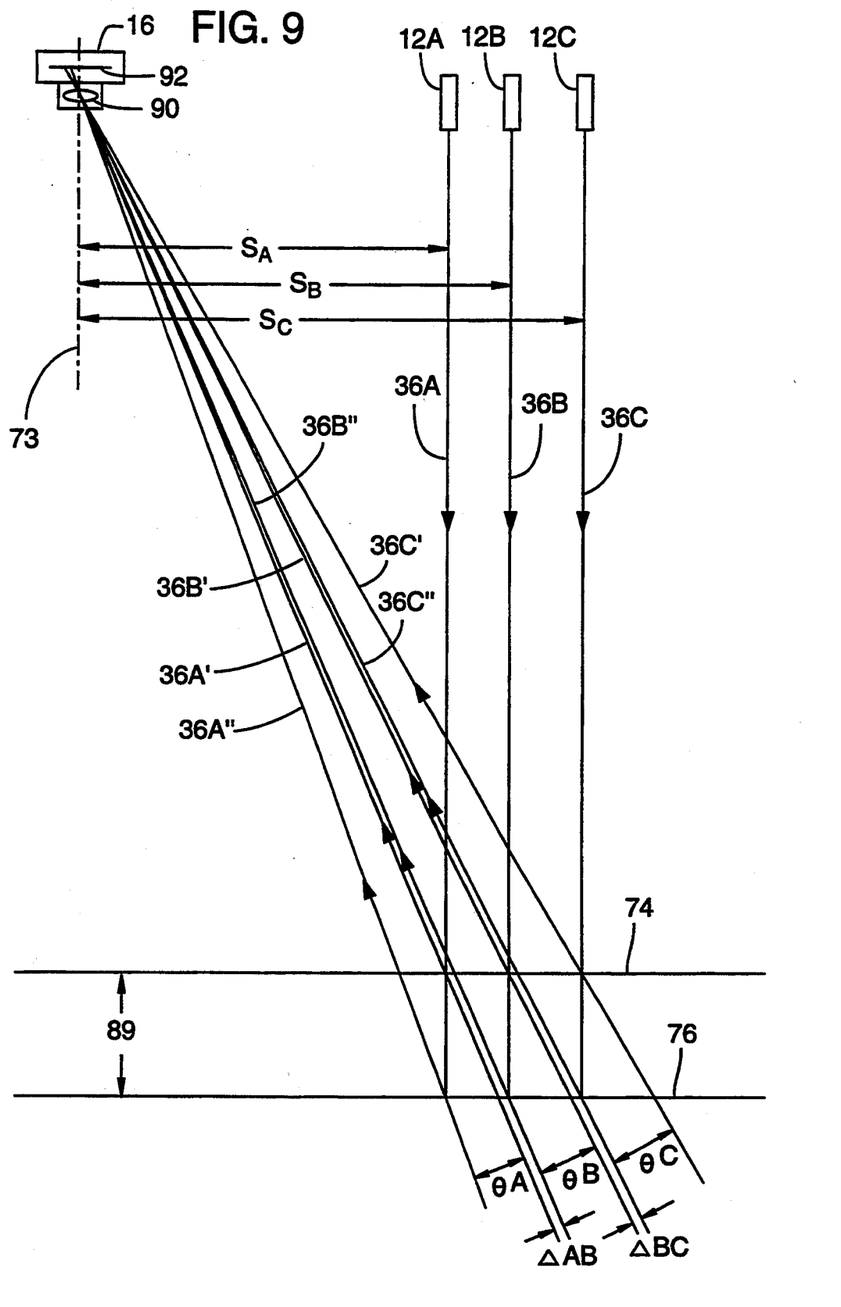
FIG. 9 is an enlarged view of a portion of the scanner of the present invention showing the spaced paths of laser light beams reflected from two objects of different thicknesses to the photoelectric sensing element of the photo-detector camera for thickness measurement.

As shown in FIGS. 7 and 9, the difference angle $\Theta$ between the reflected laser beams 36', 36" reflected from the second object surface 76 and the first object surface 74, respectively, increases with distance from the center axis 73 of the camera lens. Since the light beams in the outer portions or zones produce thickness measurements of greater accuracy, the scanner method and apparatus of the present invention selectably processes the scan data produced by the cameras giving preference to the scan data produced by laser beams in the outer field portions 56-78 and 58-80. Thus the thickness measurements do not employ the scan data produced by laser beams striking object surfaces in the inner field zones 73-78 and 73-80 unless there is defective or missing data in the data signals produced by the laser beams in the corresponding outer field portions.

As described above for camera 16B in FIG. 8, the inner portions 73-78 and 73-80 of its viewing field are also the outer portions 58-80 and 56-78 of the viewing fields of camera 16A and camera 16C. Therefore, the scanning data produced by the laser beams in zones 86, 88 and detected by the other two cameras 16A and 16B is processed by the computer system 54 to measure object thickness which enables a continuous scan of the entire length of the object to determine the configuration of such object.

It should be noted from FIG. 5 that eight laser light sources 14 are provided between each adjacent pair of cameras 18. The parallel light beams of such light sources are positioned in the camera viewing field such that four of the light beams are included in each of the inner zones 73-78 and 73-80 and four other light beams are included in each of the outer zones 56-78 and 58-80 of FIG. 8. However, these light beams have not been shown in FIG. 8 for purposes of clarity.

As shown in FIG. 9, the laser light sources 12A, 12B and 12C are properly spaced different distances from the centerline axis 73 of the camera 16 to prevent overlap of such light beams when measuring thickness differences of objects 74, 76 within the scan depth 89 of the system. The spacings $S_A$, $S_B$ and $S_C$ of laser beams 36A, 36B and 36C emitted by lasers 12A, 12B and 12C, respectively, are sufficient so that there is no overlap of the reflection beams 36', 36" reflected from the maximum and minimum thickness object planes 76 and 74.

Thus, for laser beam 36A of laser 12A the reflected beams 36A', 36A" are reflected from the object planes 76, 74, respectively, through camera lens 90 to the photoelectric target 92 of the camera 16. The reflected beams 36A', 36A" are separated by a difference angle $\Theta_A$.

The difference angle $\Theta_B$ of the reflected light beams 36B', 36B" from laser 12B is slightly greater than the difference angle $\Theta_A$ of the reflected light beams 36A', 36A" of laser 12A because laser 12B is spaced a greater distance $S_B$ from the centerline 73 of the camera lens axis than the spacing distance SA laser of 12A, as previously discussed with respect to FIG. 7. In a similar manner, the difference angle $\Theta_C$ of reflected beams 36C', 36C" of the laser 12C is greater than the difference angles of both $\Theta_B$ and $\Theta_A$ because laser 12C is spaced a greater distance $S_C$ from the centerline axis 73 of camera 16 than either of lasers 12A and 12B.

In addition, it should be noted that there is a gap spacing $\Delta AB$ between the two adjacent scan regions corresponding to difference angles $\Theta_A$ and $\Theta_B$ and a similar gap spacing $\Delta BC$ is provided between the two angles $\Theta_B$ and $\Theta_C$ so that there is no overlap on the linear diode array 92 of the camera target by the reflected laser beams corresponding to beams 36A, 36B and 36C. The gap spacings $\Delta AB$ and $\Delta BC$ are safety zones between adjacent scan regions $\Theta_A$, $\Theta_B$ and $\Theta_C$ so that two laser beams are not seen by the same portion of the camera target 92. Also, those target portions corresponding to such safety zones are not struck by any laser beam when the object being measured is within the depth of scan 89 between maximum plane 74 and minimum plane 76. Thus, the spacings $S_A$, $S_B$ and $S_C$ of the laser beams from the centerline 73 of the lens axis of camera 16 are chosen so that only one reflected laser beam can be seen by a given portion of the linear diode array of target 92 when measuring an object whose thickness is within the depth of scan 89. This provides unambiguous scan data of the object thickness which produces an accurate measure of the object thickness.

Referring again to FIG. 8, it should be noted that while the photoelectric target 92 of the camera 16B produces data signals corresponding to laser beams striking an object in the inner field portions 73–78 and 73–80 of the field of view of the camera, such scan data will be ignored by the scanner computer system 54 when determining the object thickness since such data is electronically tagged with the address of its location on the target as being in the inner portion of the viewing field by the camera interface circuit in scanner interface 52. One way of doing this tagging is by using a counter to determine the address of the scan data as shown in FIG. 10 of the above-cited Durland patent.

Figure 6:
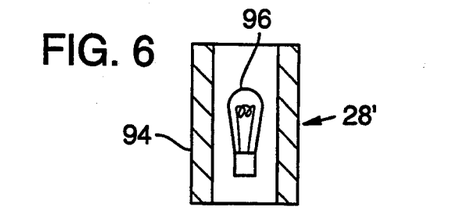
FIG. 6 is a sectional view of a second embodiment of the reference target for detecting the leading edge and the training edge of the log.

An alternative embodiment of the reference target 28 is shown in FIG. 6 as illuminated target 28' which consists of a tubular translucent plastic member 94 of Teflon or other suitable plastic, surrounding a reference light source 96 such as a halogen lamp. The light source 96 illuminates the translucent target 94 and causes it to emit light which is sensed by the camera 18 to detect the leading edge and the trailing edge of the log in a similar manner to the way it operates by sensing of the light of lasers 14 reflected from the reference targets 28 of FIG. 4. This alternative target 28' may be used when the received light of the reflected laser light beam is of insufficient intensity.

It will be obvious to those having ordinary skill in the art that many changes may be made in the above-described embodiment of the present invention without departing from the spirit of the invention. Therefore, the scope of the present invention should be determined by the following claims.

I claim:

1. Light scanner apparatus for determining the configuration of an elongated object, comprising:
   a plurality of photo-detectors spaced apart across a scanning zone through which the elongated object is moved to scan the object, each photo-detector having an optical axis and a viewing field divided by said optical axis into a right field and a left field, and each of said right and left fields having a first field portion adjacent the optical axis and a second field portion separated from the optical axis by said first field portion;
   a plurality of laser light sources positioned between said photo-detectors and supported so that at least some of the laser light beams emitted by said laser light sources are located in the viewing fields of a pair of adjacent photo-detectors and the light beams extend substantially parallel to each other and to the optical axis of each of the photo-detectors;
   mounting means for mounting the photo-detectors to cause the viewing fields of each pair of adjacent photo-detectors to overlap sufficiently so that the first field portion of one photo-detector overlaps the second field portion of the other photo-detector of said pair;
   scan signal selection means for selecting portions of a scanning output signal produced by each photo-detector when the elongated object is moved through the scanning zone, giving preference to those scanning signal portions which correspond to the second field portions of its viewing field while rejecting portions of the scanning output signal which correspond to the first field portions of said viewing field unless there is no usable signal portion corresponding to the second field portion which overlaps the first field portion; and
   signal processor means for producing an object configuration signal from the selected portions of the scanning signals of the photo-detectors which is of greater accuracy.

2. Apparatus in accordance with claim 1 in which the laser light sources are positioned in two groups on opposite sides of the scanning zone to direct light beams at the opposite sides of the elongated object during scanning.

3. Apparatus in accordance with claim 2 in which the photo-detectors are provided in cameras with lenses, said cameras being positioned in two groups on opposite sides of the scanning zone so that the elongated object is moved between said two groups of cameras during scanning.

4. Apparatus in accordance with claim 2 in which one group of laser light sources on one side of the scanning zone directs their light beams toward reference targets on the opposite side of the scanning zone to illuminate the targets which are viewed by the photo-detectors on said one side of the scanning zone and to block said targets from the view of the photo-detectors by the object to detect the leading edge and trailing edge of the object as it is moved laterally through the scanning zone.

5. Apparatus in accordance with claim 1 in which the laser light beams are reflected off the surface of the elongated object to the photo-detectors for measuring the distance from the photo-detectors to the surface of said object to produce the scanning signals, and the scan signal selection means and the signal processor means are provided by a digital computer which determines the surface configuration of the object from the selected signal portions.

6. Apparatus in accordance with claim 5 which also includes a plurality of non-coherent light sources spaced along the scanning zone for illuminating the elongated object with non-coherent polychromatic light of lower intensity than the laser light, and at least some of said photo-detectors detecting the non-coherent light reflected from said object to sense the end of the object and determine the length of said object.

7. Apparatus in accordance with claim 4 in which the reference targets are made of translucent plastic material.

8. Apparatus in accordance with claim 7 in which the reference targets are translucent plastic tubes with light bulbs positioned in said tubes to illuminate the tubes.

9. Apparatus in accordance with claim 1, in which the elongated object is a log and which also includes charger arms positioned between the laser light beams for gripping the log and moving it laterally through the scanning zone during scanning.

10. A method for scanning an elongated object, such as a log, to determine the configuration of said elongated object, comprising the steps of:
positioning a plurality of photo-detectors spaced apart across a scanning zone, said photo-detectors each having an optical axis and a viewing field divided by the optical axis into a right field and a left field which each have a first field portion adjacent the optical axis and a second field portion separated from the optical axis by the first field portion;
aligning said photo-detectors to cause the viewing fields of each pair of adjacent photo-detectors to overlap so that the first field portion of one photo-detector overlaps the second field portion of the other photo-detector of said pair;
positioning a plurality of laser light sources between said photo-detectors so that the laser light beams emitted by said laser light sources each has its beam axis located in the viewing fields of a pair of adjacent photo-detectors and the beam axes extend substantially parallel to each other and to the optical axis of the other laser light beams;
moving the elongated object relative to the laser light sources and the photo-detector through said scanning zone to scan said elongated object and produce a scanning output signal at the output of each photo-detector;
selecting those portions of the scanning output signals which correspond to the second field portions of the viewing fields of the photo-detectors, and rejecting those portions of the scanning output signals which correspond to the first field portions of said viewing fields unless there is no usable signal portion corresponding to the second field portion which overlaps the first field portion; and
combining the selected portions of the scanning output signals to produce an object configuration signal.

11. A method in accordance with claim 10 in which the laser light sources are positioned in two groups on opposite sides of the scanning zone, and the moving step moves the elongated object between said two groups of laser light sources to direct laser light beams at the opposite sides of the elongated object during scanning.

12. A method in accordance with claim 11 in which the photo-detectors are in separate cameras having lenses positioned in two groups on opposite sides of the scanning zone and the elongated object is moved between said two groups of cameras during scanning.

13. A method in accordance with claim 11 which also includes the step of directing at least some of the laser light beams from light sources on one side of the scanning zone across said zone toward reference targets on the opposite side of the scanning zone which are viewed by photo-detectors on said one side of the scanning zone to detect the leading edge and the trailing edge of the elongated object as it move through said zone.

14. A method in accordance with claim 10 including the step of reflecting the laser light beams off the surface of the elongated object to the photo-detectors to produce the scanning output signals which are used to determine the surface configuration of said object.

15. A method in accordance with claim 14 which also includes the steps of illuminating the elongated object with non-coherent polychromatic light and detecting at least some of the non-coherent light reflected from the object with photo-detectors to sense the end of the object and produce a corresponding non-coherent light scanning signal.

16. A method in accordance with claim 10 in which the elongated object is a log and is moved during scanning by charger arms positioned between the laser light beams and gripping the side of the log.

17. A method in accordance with claim 15 in which the non-coherent light is of lower intensity than the laser light and the non-coherent light scanning signal is combined with the laser light scanning pulses which are of higher amplitude to provide a combined scanning output signal.

18. A method in accordance with claim 14 in which the photo-detectors each have a linear array of diodes as its photoelectric sensor to detect the reflected laser light beam for measuring the distance from the sensor to the elongated object.

19. A method in accordance with claim 18 in which the photo-detector is a camera having a lens which focusing the sensor so that different portions of the linear array of diodes are focused on different laser light beams over the depth of field of the lens with each array portion focused on only one laser light beam.

20. A method in accordance with claim 10 in which the elongated object is a log which is moved through the scanning zone by charger arms.

* * * * *